(12) United States Patent
Astratov

(10) Patent No.: US 9,411,103 B2
(45) Date of Patent: Aug. 9, 2016

(54) CONTACT FOCUSING HOLLOW-CORE FIBER MICROPROBES

(71) Applicant: Vasily N. Astratov, Charlotte, NC (US)

(72) Inventor: Vasily N. Astratov, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 255 days.

(21) Appl. No.: 14/106,221

(22) Filed: Dec. 13, 2013

(65) Prior Publication Data

US 2015/0316717 A1 Nov. 5, 2015

Related U.S. Application Data

(63) Continuation-in-part of application No. 13/321,965, filed on Nov. 22, 2011, now Pat. No. 8,554,031.

(60) Provisional application No. 61/878,285, filed on Sep. 16, 2013.

(51) Int. Cl.
*G02B 6/32* (2006.01)
*A61B 18/22* (2006.01)
(Continued)

(52) U.S. Cl.
CPC ............... *G02B 6/262* (2013.01); *A61B 18/22* (2013.01); *G02B 1/00* (2013.01); *G02B 6/32* (2013.01); *A61B 2018/2227* (2013.01); *A61B 2018/2266* (2013.01); *G02B 1/005* (2013.01); *G02B 6/02304* (2013.01); *G02B 6/02328* (2013.01);
(Continued)

(58) Field of Classification Search
CPC ............... A61B 2018/2266; A61B 2018/2227
See application file for complete search history.

(56) References Cited

U.S. PATENT DOCUMENTS 3,843,865 A * 10/1974 Nath .................. B23K 26/0096
219/121.6
4,398,790 A * 8/1983 Righini .................. A61B 18/22
385/33
(Continued)

FOREIGN PATENT DOCUMENTS

JP 2002040277 A * 2/2002
JP 2004279797 A * 10/2004

OTHER PUBLICATIONS

Matsuura et al. ("Small-bore hollow waveguide for delivery of near singlemode IR laser radiation", Electronics Letters, vol. 30, No. 20, pp. 1688-1690, Sep. 29, 1994).*

(Continued)

*Primary Examiner* — Michelle R Connelly
(74) *Attorney, Agent, or Firm* — Clements Bernard PLLC; Christopher L. Bernard; Lawrence A. Baratta, Jr.

(57) ABSTRACT

A focusing microprobe system, comprising: one of a single-mode laser radiation source and a few-mode laser radiation source; a coupler coupled to the laser radiation source; one of a single-mode flexible laser radiation delivery system and a few-mode flexible laser radiation delivery system coupled to the coupler; and one or more focusing microlenses coupled to the flexible laser radiation delivery system and arranged in a focusing tip. The coupler comprises a focusing lens. The flexible laser radiation delivery system comprises one of a hollow-core fiber and a flexible waveguide. Optionally, the one or more focusing microlenses are bonded to seal a hollow internal cavity of the flexible laser radiation delivery system. The one or more focusing microlenses comprise one or more conventional lenses or one or more focusing spheres, hemispheres, or cylinders.

19 Claims, 3 Drawing Sheets

(51) Int. Cl.
  *G02B 6/26*      (2006.01)
  *G02B 6/032*     (2006.01)
  *G02B 6/42*      (2006.01)
  *G02B 1/00*      (2006.01)
  *G02B 6/02*      (2006.01)

(52) U.S. Cl.
  CPC . *G02B 6/032* (2013.01); *G02B 6/42* (2013.01); *G02B 6/4206* (2013.01)

(56) References Cited

U.S. PATENT DOCUMENTS

| | | | | |
|---|---|---|---|---|
| 4,671,609 A | * | 6/1987 | Khoe | G02B 6/4203 359/900 |
| 5,782,825 A | * | 7/1998 | Anderson | A61B 18/24 606/15 |
| 6,104,853 A | * | 8/2000 | Miyagi | A61B 18/22 385/125 |
| 6,620,154 B1 | * | 9/2003 | Amirkhanian | A61B 18/22 385/34 |
| 2009/0052849 A1 | * | 2/2009 | Lee | A61B 5/0084 385/119 |
| 2011/0251603 A1 | * | 10/2011 | Temelkuran | A61B 18/201 606/16 |
| 2012/0157979 A1 | * | 6/2012 | Li | A61B 18/24 606/15 |

OTHER PUBLICATIONS

Yang et al. ("Photonic nanojet-induced modes in chains of size-disordered microspheres with an attenuation of only 0.08 dB per sphere", Applied Physics Letters 92, 2008, pp. 261111-1 through 261111-3).*

* cited by examiner

CONTACT FOCUSING HOLLOW-CORE FIBER MICROPROBES

CROSS-REFERENCE TO RELATED APPLICATION(S)

The present patent application/patent claims the benefit of priority of co-pending U.S. Provisional Patent Application No. 61/878,285, filed on Sep. 16, 2013, and entitled "CONTACT FOCUSING HOLLOW-CORE FIBER MICROPROBES," the contents of which are incorporated in full by reference herein. The present patent application/patent is a continuation-in-part of co-pending U.S. patent application Ser. No. 13/321,965 (now U.S. Pat. No. 8,554,031), filed on Nov. 22, 2011, and entitled "FOCUSING MULTIMODAL OPTICAL MICROPROBE DEVICES," the contents of which are also incorporated in full by reference herein.

STATEMENT OF GOVERNMENT SUPPORT

The present invention was made with U.S. Government support under Award No. W911NF-09-1-0450 by the Army Research Office and Award No. ECCS-0824067 by the National Science Foundation. Accordingly, the U.S. Government may have certain rights in the present invention.

FIELD OF THE INVENTION

The present invention relates generally to the optics and medical fields. More specifically, the present invention relates to contact focusing hollow-core fiber microprobes and the like.

BACKGROUND OF THE INVENTION

Focusing microprobes, or "laser scalpels," are used in many applications, such as medical applications, where an intense laser beam needs to be delivered to and tightly focused at the surface of specimen or tissue. There are several important requirements associated with such focusing microprobes.

First, in many applications, the laser radiation needs to be delivered using a flexible waveguide system or the like, where the laser beam is isolated from the surrounding medium. For example, this is required in some surgical procedures performed in sensitive tissues, such as brain surgeries, ultraprecise intraocular surgeries, and the like. In particular, this is important when using wavelengths that are readily absorbed by the sensitive tissues, such as the emission wavelength of an Er:YAG laser ($\lambda$=2.94 µm). Flexible optical delivery is also required in applications where the path of the optical beams needs to be curved in space because of geometrical or mechanical restrictions, such as in biomedical spectroscopy applications and the like. The use of flexible optical delivery systems typically leads to additional optical losses and to reduced quality of the optical beams.

Second, for focusing microprobes, systemic optical losses must be minimized. There are many factors contributing to optical losses in such systems, including coupling losses between a source and the flexible optical delivery system, coupling losses in a focusing tip, absorption, scattering and reflection, and other factors. In addition, a large power transmission is typically required in applications such as ultraprecise laser surgery, micro-welding, bonding, and surface patterning, compounding the systemic optical loss problem.

Third, for focusing microprobes, the diameter of the focused laser beam at the tip of the microprobe must be minimized in order to provide more localized laser action. In the case of ultraprecise laser surgery, for example, this is required to minimize the size of ablation craters in the tissue.

Fourth, in many applications, the microprobe must be able to operate in contact or in near contact with the tissue or other specimen. In some applications, this is required due to strong absorption of the laser radiation by the surrounding medium. It can also make the surgery or other procedure easier and more efficient to perform.

Finally, the design of such microprobes involves a trade-off between the total transmitted power and the diameter of the focal spot. One approach to the design of such microprobes is based on using multi-modal delivery systems. These multi-modal delivery systems usually guide hundreds of modes and tend to favor high total transmitted power at the expense of focal spot size. Another approach to the design of such microprobes is based, in part, on using single-mode or few-mode delivery components. The definition of a few-mode system is not precise, but for the purposes of the present invention, fibers with $3<V<10$, where $V=2\pi a(NA)/\lambda$, are considered few-mode. In this definition, a is the radius of the core, NA is the numerical aperture, and $\lambda$ is the wavelength of light. The condition for single-mode operation is $V<2.405$. The definition of few-mode fibers implies that the core of the waveguiding system is slightly wider than that required by the single-mode cut-off condition. As a result, a few modes are guided by the system, however, this number is very limited, typically in 2-6 range. The main focus of the present invention is on single-mode systems. However, the general approach can be extended to few-mode systems. Single and few-mode systems usually allow much better focusing as compared to multi-mode systems, but they require single-mode laser radiation sources for efficient operation. The classical single-mode delivery component is represented by a conventional single-mode fiber. However, such fibers are not well developed for the mid-IR ranges of wavelengths required for some applications, such as a contact laser surgery.

Thus, the present invention utilizes a flexible laser radiation delivery system, i.e. a hollow-core fiber. This delivery system has sufficiently large core diameter, simplifying the coupling of single-mode or few-mode laser emissions into such cores. On the other hand, as a delivery system, it still operates in a close to single-mode regime that is important for achieving tight beam focusing. The system of the present invention provides a unique solution for flexible laser radiation delivery combined with tight focusing in cases where conventional single-mode fibers are not available or may not be used. The system of the present invention allows for a continuous single-mode (or few-mode) design all the way from the laser radiation source to actual application in tissue or other media. This is novel and this design provides critical advantages over other designs in cases where compact and portable single-mode laser radiation sources must be used with very high efficiency for producing tightly focused beams.

BRIEF SUMMARY OF THE INVENTION

In various exemplary embodiments, the present invention provides systems and methods for the flexible optical delivery to and focusing of electromagnetic (i.e. laser) radiation at the surface of a sample, specimen, tissue, etc. The focusing microprobes utilize a single-mode or multi-mode laser source, a hollow-core fiber delivery system, and a focusing tip. The hollow-core fiber provides for flexible and efficient delivery of the single-mode or multi-mode laser radiation to the focusing tip. The focusing tip includes a lens, such as a (dielectric) microsphere or several (dielectric) microspheres assembled in a linear chain. The tip focuses the laser radiation down to diffraction limited beam diameters in a contact mode or near-contact mode, thereby providing high optical throughput and satisfying the requirements associated with ultraprecise laser surgery, micro-welding, bonding, surface patterning, and the like.

In one exemplary embodiment, the present invention provides a focusing microprobe system, comprising: one of a single-mode laser radiation source and a few-mode laser radiation source; a coupler coupled to the laser radiation source; one of a single-mode flexible laser radiation delivery system and a few-mode flexible laser radiation delivery system coupled to the coupler; and one or more focusing microlenses coupled to the flexible laser radiation delivery system and arranged in a focusing tip. The coupler comprises a focusing lens. The flexible laser radiation delivery system comprises one of a hollow-core fiber and a flexible waveguide. Optionally, the hollow-core fiber comprises a microstructured fiber comprising a negative curvature core wall. Optionally, the hollow-core fiber comprises a photonic crystal fiber. Optionally, the one or more focusing microlenses are bonded to seal a hollow internal cavity of the flexible laser radiation delivery system. The one or more focusing microlenses comprise one or more conventional lenses or one or more focusing spheres, hemispheres, or cylinders. The one or more focusing spheres, hemispheres, or cylinders are made of a dielectric material. Optionally, the one or more focusing microlenses comprise a plurality of focusing microlenses arranged in a linear chain. Optionally, the plurality of focusing microlenses arranged in a linear chain comprise focusing microlenses of varying size. Optionally, the plurality of focusing microlenses arranged in a linear chain comprise focusing microlenses of varying index of refraction. Optionally, the plurality of focusing microlenses arranged in a linear chain comprise focusing microlenses that are in direct physical contact. Optionally, the one or more focusing microlenses are integrated into the flexible laser radiation delivery system.

In another exemplary embodiment, the present invention provides a method for providing a focusing microprobe system, comprising: providing one of a single-mode laser radiation source and a few-mode laser radiation source; providing a coupler coupled to the laser radiation source; providing one of a single-mode flexible laser radiation delivery system and a few-mode flexible laser radiation delivery system coupled to the coupler; and providing one or more focusing microlenses coupled to the flexible laser radiation delivery system and arranged in a focusing tip. The coupler comprises a focusing lens. The flexible laser radiation delivery system comprises one of a hollow-core core fiber and a flexible waveguide. Optionally, the hollow-core fiber comprises a microstructured fiber comprising a negative curvature core wall. Optionally, the hollow-core fiber comprises a photonic crystal fiber. Optionally, the one or more focusing microlenses are bonded to seal a hollow internal cavity of the flexible laser radiation delivery system. The one or more focusing microlenses comprise one or more conventional lenses or one or more focusing spheres, hemispheres, or cylinders. The one or more focusing spheres, hemispheres, or cylinders are made of a dielectric material. Optionally, the one or more focusing microlenses comprise a plurality of focusing microlenses arranged in a linear chain. Optionally, the plurality of focusing microlenses arranged in a linear chain comprise focusing microlenses of varying size. Optionally, the plurality of focusing microlenses arranged in a linear chain comprise focusing microlenses of varying index of refraction. Optionally, the plurality of focusing microlenses arranged in a linear chain comprise focusing microlenses that are in direct physical contact. Optionally, the one or more focusing microlenses are integrated into the flexible laser radiation delivery system.

BRIEF DESCRIPTION OF THE DRAWINGS

The present invention is illustrated and described herein with reference to the various drawings, in which like reference numbers are used to denote like system components/method steps, as appropriate, and in which.

DETAILED DESCRIPTION OF THE INVENTION

Figure 1:
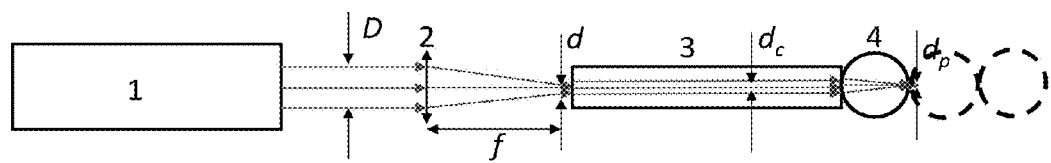
FIG. 1 is a schematic diagram illustrating one exemplary embodiment of the focusing microprobe of the present invention.

Referring now specifically to FIG. 1, in one exemplary embodiment, the focusing microprobe of the present invention includes a laser radiation source (1), a focusing lens (2), a flexible optical delivery system (3), and one or more microlenses (4) assembled as a focusing tip. For efficient coupling of the source to the delivery system, two main conditions must be satisfied. First, the diameter, d, of the focused laser beam at the edge of the delivery system (either fiber or waveguide) must be smaller than the diameter of the core, $d_c$, of the delivery system. The focused beam diameter can be approximated by the formula:

$$d=M^2\lambda/(2NA_i),$$

where $M^2$ is a laser beam quality number indicating how close the laser beam is to being a single-mode beam and $NA_i=n\sin\theta_i\approx nD/(2f)$ is the numerical aperture of the incident laser beam, n is the index of the medium (n=1 in air), $\theta_i$ is the angle of incidence, D is the diameter of the laser beam, and f is the focal distance of the lens. The second condition for efficient coupling is that the cone of incident light must be within the acceptance cone of the delivery system, $NA_i \leq NA_{del}$.

Figure 2:
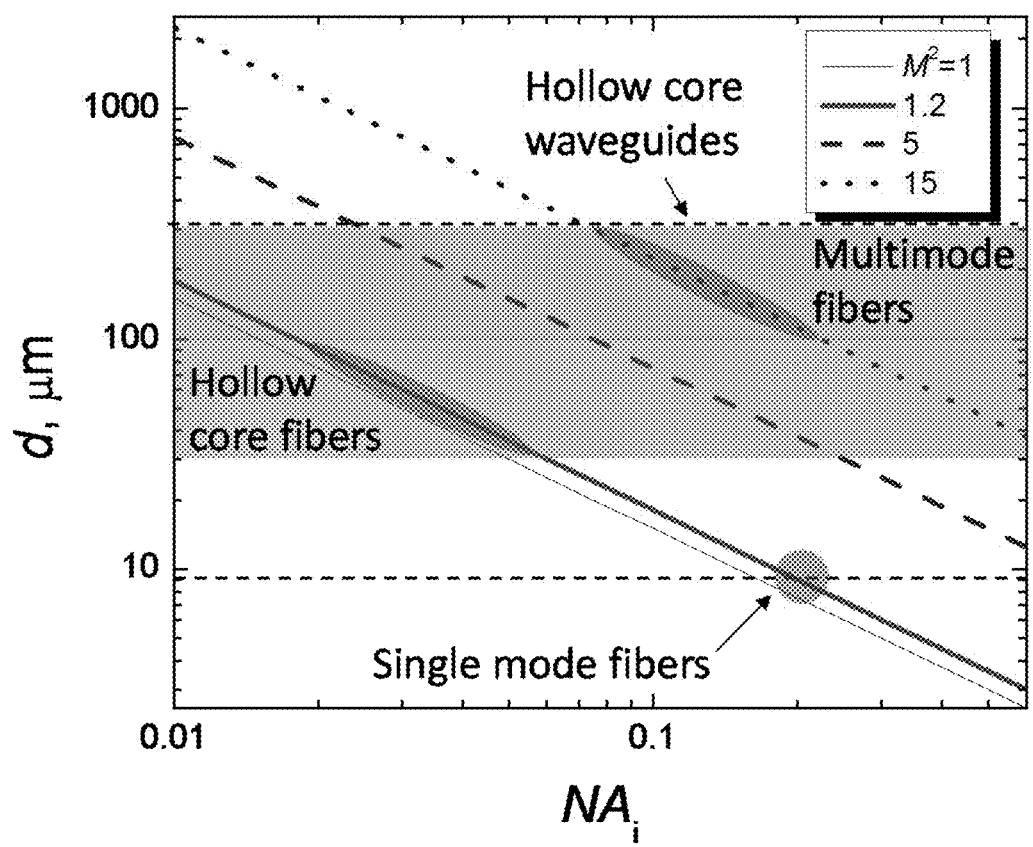
FIG. 2 is a plot illustrating the dependence of input beam diameter (d) on its numerical aperture (NA) for laser beams with different beam quality factors $M^2=1$, 1.2, 5, and 15 at $\lambda=2.94$ μm, with efficient coupling to multi-mode fibers ($M^2=15$) expected at $100<d<300$ μm and $0.1<NA_i<0.2$, efficient coupling to single-mode fibers ($M^2=1.2$) expected at $d\approx 9$ μm and $NA_i\approx 0.2$, and efficient single-mode ($M^2=1.2$) coupling to hollow core fibers expected at $30<d<100$ μm and $0.02<NA_i<0.06$.

Coupling efficiency of the source to the delivery system is analyzed based on the above equation, as illustrated for $\lambda=2.94$ μm in FIG. 2. The lines in this plot illustrate the relationships between d and $NA_i$ for a laser beam focused at the edge of the delivery system. The quality of the input beam is varied in the $1\leq M^2 \leq 15$ range. The single-mode laser source is represented by $M^2=1$, however in most practical cases, this number is slightly higher than unity, such as, for example, $M^2=1.2$. The multi-modal sources are represented by $M^2 \gg 1$. As illustrated in FIG. 2, the coupling of light from the multi-modal source ($M^2=15$) into a multi-modal delivery system is a relatively simple task, due to the large core diameters of the fibers and hollow waveguides. For example, the typical diameters of the cores of the multi-modal fibers for $\lambda=2.94$ μm are within the ~100-300 μm range. The typical diameters of the hollow-core waveguides used in the same spectral range are about 300 μm. Efficient coupling to such cores also requires sufficiently large numerical apertures, $NA_{del}$~0.1-0.2, which are generally available in such multi-modal delivery systems with $M^2$=15.

The use of multi-modal systems provides very simple and efficient delivery of electromagnetic energy to the tip of the microprobe. However, the sharp focusing of such multi-modal beams provided by the lens is not possible conventionally, as each mode tends to be focused individually. All these focused beams are shifted in space and only partly overlapped, leading to a significant broadening of the resulting beam. Thus, a multi-mode fiber or hollow waveguide integrated with a single lens or microsphere results in relatively small coupling and propagation losses, but often cannot be used for achieving compact diameters, $d_p$, of the beam at the tip of the microprobe.

Sharper focusing of multi-modal input beams can be achieved by using chains of microspheres, which are capable of filtering periodically focused modes. It has been demonstrated that optimally designed chains of microspheres with an index 1.65<n<1.75 can be used for reducing the diameters of the focused beams at the tip of the end microsphere. Generally, there is a tradeoff between, $d_p$, and the power contained in the focused beam. The chains of microspheres can provide a reduction of the focal spot sizes for multi-modal input beams at the expense of the transmitted power.

Further reduction of the losses and dimensions of the focal beams becomes possible using a single-mode or few-mode laser source. Such single-mode emission can be transmitted by a single-mode waveguide and focused down to diffraction limited dimensions at the surface of the sample or tissue. However, the realization of such single-mode or few-mode systems presents certain technical challenges, as is described herein below.

The coupling of a single-mode source to a single-mode fiber is illustrated in FIG. 2 for λ=2.94 μm by a circle corresponding to d=9 μm and NA~0.2. The single-mode beam can be focused down to diffraction limited dimensions by a spherical or hemispherical microprobe tip. However, use of single-mode fibers is very complicated in many applications. First, achieving efficient coupling of light to such small single-mode cores (d=9 μm) requires extremely precise beam positioning and alignment. Although possible in research laboratories, such levels of precision can be impractical in clinical and industrial environments. Second, for some spectral ranges, such as at λ~3 μm, the technology of single-mode fibers is not well developed and they are not readily available as commercial products. Thus, although the use of single-mode lasers in combination with single-mode fibers, in principle, allows for highly efficient microprobes with small spot sizes, the practical realization of such devices is impeded by technical limitations.

It should be noted that the single-mode beams can be focused to dimensions even smaller than the classical diffraction limit. There are many approaches using polarization effects and novel metamaterials that have been used for achieving such super tight focusing. Examples include the use of radially polarized beams, solid-immersion lenses, near-field probes, negative index materials, plasmon gratings, and hyperbolic metamaterials. The application of these methodologies in contact focusing microprobes has been impeded by various technical limitations, including light absorption and losses, limed spectral ranges of operation, challenging fabrication, and other factors. These methodologies allow for increasing the resolution of optical systems beyond the classical diffraction limit, but usually only a small fraction of the power of the source can be coupled to nanoscale beams. Thus, these methodologies are not suitable for high power applications, where conventional lenses still remain the focusing elements of choice.

Figure 3:
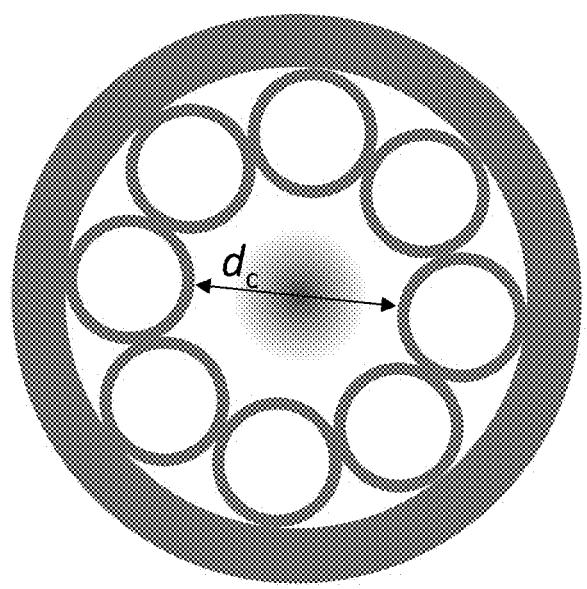
FIG. 3 is a schematic diagram illustrating an exemplary hollow-core microstructured optical fiber with cladding formed by one row of capillaries, wherein the optical mode is confined in a central hollow region with an effective air core diameter, $d_c$.

Exemplary embodiments of the present invention utilize hollow-core fibers as the single-mode or few-mode flexible optical delivery system. Hollow-core photonic crystal fibers and hollow-core microstructured optical fibers are relatively new forms of optical fiber waveguide with unique properties. A schematic image of an optical mode guided by a hollow-core fiber without a photonic band gap, but with a negative curvature core wall, is illustrated in FIG. 3. These hollow-core fibers provide a combination of the following properties: a) single-mode or few-mode transmission; b) losses <0.1 dB/m; c) very large core diameters as compared to conventional single-mode fibers; and d) relatively small values of $NA_{del}$ as compared to conventional single-mode fibers. For example, the effective air core diameter of such hollow-core fibers can be in the range of 30<$d_c$<100 μm for λ~3 μm.

Hollow-core fibers provide the conditions for efficient light coupling from single-mode or few-mode laser sources and delivery and focusing at the surface of the sample or tissue. The conditions for the efficient coupling of single-mode lasers ($M^2$~1.2) to hollow-core fibers take place at 30<$d_c$<100 μm and 0.02<$NA_i$<0.06, as is illustrated in FIG. 2. Due to large core diameters, such coupling is much simpler and more robust than coupling with conventional single-mode fibers. In addition, there is no surface reflection at the edge of the core as compared to conventional fibers, additionally reducing the coupling losses. This coupling does not require extremely precise alignment of the input beam and can be easily provided in a clinical or industrial environment. The propagation losses of hollow-core fibers are usually higher than those of conventional fiber or waveguides systems; however, they are sufficiently small for developing applications in contact focusing microprobes. For example, the length of the delivery system required in laser surgery applications is on the order of 2 m, which means that the propagation losses can be bounded by 0.2 dB, which is an acceptable level of loss.

Finally, due to its single-mode properties, the beam delivered by the hollow-core fibers can be focused down to diffraction limited dimensions. This focusing can be performed by a lens, such as a dielectric microsphere or linear chain of dielectric microspheres. For focusing beams in a contact or near-contact conditions, spheres with a sufficiently high index of refraction 1.65<n<1.80 can be used. One example of a material with good optical quality for mid-IR applications is a sapphire sphere with n=1.71 at λ=2.94 μm. A single sphere can be glued or fixed at the output edge of the hollow-core fiber, for example.

In order to further reduce the focal beam diameter, the spheres can be assembled as a chain and integrated with the hollow-core fiber. Such chains filter periodically focused modes with radial polarization. Radially polarized beams can be focused to dimensions smaller than the diffraction limit.

The focusing microprobe of the present invention may be used in ultraprecise surgeries that require very shallow depths of tissue cutting. For example, this is required for dissecting and removing unhealthy fibrotic membranes formed at the back of the eye near the retina. These membranes can develop as the result of diabetic retinopathy or other medical conditions, and they can significantly reduce the vision or even completely block the sight in some cases. These membranes are extremely thin and strongly attached to the retina. One of the requirements of such surgeries is to protect the retina underneath these membranes. This requires extremely shallow cut depths which can be achieved using the proposed contact microprobe with controllable ~10-30 μm cutting depth. Due to its compact size, the focusing microprobe of the present invention can be easily integrated with existing surgical tools, such as grabbing instruments, and with imaging devices.

It should be noted that, in recent years, a new generation of diode pumped Er:YAG lasers has appeared on market. These lasers are extremely compact, easy to operate, and very inexpensive. Some of these lasers operate in single-mode or few-mode regimes. These laser sources can be integrated with the contact focusing microprobes of the present invention to produce portable and inexpensive systems for ultraprecise surgery. Vitreoretinal surgery is currently performed using a combination of mechanical tools; however, these tools are not entirely safe and sometimes result in bleeding and postoperative complications. Use of the proposed contact focusing microprobes results in easier and safer vitreoretinal surgery. In addition, the laser radiation sources utilized can be modulated at relatively high frequency, ~$10^3$ Hz. This allows for very fast tissue cutting that results in the reduction of the surgical time compared to conventional procedures.

One of the important advantage of the proposed microprobes is their single-mode (or few-mode) design all the way from the laser radiation source to tissue application. This single-mode design makes it possible to combine high throughput with sharp focusing in combination with flexible delivery. Another important advantage of this design is the fact that a single-mode beam does not require a complicated focusing system for achieving sharp focusing. In contrast with previously developed multi-modal microprobes, the proposed devices can operate with a single sphere attached at the end of the flexible delivery system. This sphere would naturally occupy the axially aligned position at the edge of the hollow-core fiber, for example. The fixing of this sphere at this position can be achieved by gluing it using an epoxy or other liquid or semi-liquid material with an ability to solidify.

It is very important to stress that the structure of microcapillaries can be easily sealed in the process of fixing sphere(s) of the present invention. This makes the internal structure of the microprobes well protected from the external environment. For this reason, the proposed microprobes can operate inside a liquid environment essentially without significant change in focusing characteristics. For example, if the index of the sphere is selected to provide a sharp focusing at its tip, this property will be preserved after immersing the tip of the device in a liquid or in tissue. It is well known that in paraxial approximation the focusing of the collimated beam is provided exactly at the tip of the sphere with a refractive index, n=2.0. In the proposed microprobe, the focusing can be provided far from paraxial conditions with the best results expected for indices in the 1.65-1.8 range. Such spheres are readily available for these applications with the examples represented by the sapphire and ruby spheres.

Another potential market is based on developing applications in cellular surgery and in cells research. The proposed systems and methods can be used for making tiny holes in cell membranes that can be used for delivering drugs inside the cells. Sometimes, conventional microscopes are used for this purpose. This procedure has been termed photoporation of cells. The advantage of the proposed systems and methods is that the probe can be micromanipulated to reach areas that are difficult to access by conventional techniques.

One more potential market is based on micro-welding, optical bonding, and surface photo-patterning applications, where very local delivery of the optical power is required in a contact or near-contact mode.

Ultraprecise surgery can be performed using lasers at a wavelength where the tissue is transparent or partly transparent. Such systems are extremely well developed and used, for example, in LASIK surgery. In such systems, a surgical effect is achieved due to the concentration of electromagnetic energy at the focal point inside the tissue. For example, these systems are well suited for making very precise plane-parallel cuts through ophthalmic tissue like in the case of LASIK surgery. For some surgeries, however, these laser systems cannot be deployed. For example, as described herein above, removing fibrotic membranes from the retina requires more precise contact tools because these membranes are extremely thin and their surface is uneven. A contact laser scalpel with extremely shallow surgical action would be a perfect tool for dissecting and removing such fibrotic membranes.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A focusing microprobe system, comprising:
   one of a single-mode laser radiation source and a few-mode laser radiation source;
   a coupler engaging the laser radiation source;
   one of a single-mode flexible laser radiation delivery system and a few-mode flexible laser radiation delivery system enaging the coupler; and
   a plurality of adjacent focusing microlenses arranged in a linear chain coupled to the flexible laser radiation delivery system and arranged in a focusing tip, wherein one or more of the plurality of adjacent focusing microlenses has a high index of refraction of equal to or greater than 1.7.

2. The focusing microprobe system of claim 1, wherein the coupler comprises a focusing lens.

3. The focusing microprobe system of claim 1, wherein the flexible laser radiation delivery system comprises one of a hollow-core fiber and a flexible waveguide.

4. The focusing microprobe system of claim 3, wherein the hollow-core fiber comprises a microstructured fiber comprising a negative curvature core wall.

5. The focusing microprobe system of claim 3, wherein the hollow-core fiber comprises a photonic crystal fiber.

6. The focusing microprobe system of claim 1, wherein one or more of the plurality of adjacent focusing microlenses are bonded to seal a hollow internal cavity of the flexible laser radiation delivery system.

7. The focusing microprobe system of claim 1, wherein the plurality of adjacent focusing microlenses comprise a plurality of focusing spheres, hemispheres, or cylinders.

8. A method for providing a focusing microprobe system, comprising:
   providing one of a single-mode laser radiation source and a few-mode laser radiation source;
   providing a coupler engaging the laser radiation source;
   providing one of a single-mode flexible laser radiation delivery system and a few-mode flexible laser radiation delivery system engaging the coupler; and
   providing a plurality of adjacent focusing microlenses arranged in a linear chain coupled to the flexible laser radiation delivery system and arranged in a focusing tip, wherein one or more of the plurality of adjacent focusing microlenses has a high index of refraction of equal to or greater than 1.7.

9. The focusing microprobe method of claim 8, wherein the coupler comprises a focusing lens.

10. The focusing microprobe method of claim 8, wherein the flexible laser radiation delivery system comprises one of a hollow-core fiber and a flexible waveguide.

11. The focusing microprobe method of claim 10, wherein the hollow-core fiber comprises a microstructured fiber comprising a negative curvature core wall.

12. The focusing microprobe method of claim 10, wherein the hollow-core fiber comprises a photonic crystal fiber.

13. The focusing microprobe method of claim 8, wherein one or more of the plurality of adjacent focusing microlenses are bonded to seal a hollow internal cavity of the flexible laser radiation delivery system.

14. The focusing microprobe method of claim 8, wherein the plurality of adjacent focusing microlenses comprise a plurality of focusing spheres, hemispheres, or cylinders.

15. A focusing microprobe system, comprising:
   one of a single-mode laser radiation source and a few-mode laser radiation source;
   a coupler engaging the laser radiation source;
   one of a single-mode flexible laser radiation delivery system and a few-mode flexible laser radiation delivery system enaging the coupler; and
   one or more focusing microlenses coupled to the flexible laser radiation delivery system and arranged in a focusing tip, wherein each of the one or more focusing microlenses has a high index of refraction of equal to or greater than 1.7 such that the focusing microprobe system can be used with the one or more focusing microlenses in contact with an external object.

16. The focusing microprobe system of claim 15, wherein the coupler comprises a focusing lens.

17. The focusing microprobe system of claim 15, wherein the flexible laser radiation delivery system comprises one of a hollow-core fiber and a flexible waveguide.

18. The focusing microprobe system of claim 15, wherein the one or more focusing microlenses are bonded to seal a hollow internal cavity of the flexible laser radiation delivery system.

19. The focusing microprobe system of claim 15, wherein the one or more focusing microlenses comprise one or more focusing spheres, hemispheres, or cylinders.

* * * * *